United States Patent [19]

Stephas

[11] 3,973,251
[45] Aug. 3, 1976

[54] TIMING DEVICE FOR EXERCISE PROGRAM WITH SIGNALLING MEANS

[76] Inventor: J. Larry Stephans, 216-30 117th Road, Cambria Heights, N.Y. 11411

[22] Filed: Apr. 25, 1975

[21] Appl. No.: 571,643

[52] U.S. Cl. .............................. 340/309.1; 272/69; 272/73; 200/38 B; 340/309.4; 128/2.06 R
[51] Int. Cl.² .......................................... G08B 1/00
[58] Field of Search.......... 340/309.1, 309.2, 309.3, 340/309.4; 128/2.06 R, 208; 272/69, 73; 58/9, 21.16, 130, 145; 200/27 B, 38 B; 307/139

[56] References Cited
UNITED STATES PATENTS
3,735,101  5/1973  Stewart ........................... 340/309.4

Primary Examiner—John W. Caldwell
Assistant Examiner—William M. Wannisky
Attorney, Agent, or Firm—Spencer E. Olson

[57] ABSTRACT

A physiotherapy timing and control device for instructing a patient to perform a prescribed program of exercise including a series of "exercise" periods each followed by a "rest" period at the start of which the patient is required to read and record his pulse, includes a spring-wound timer having a dial time-graduated in intervals corresponding to the periods of the exercise program to provide visual guidance concerning the progress of the program, and signal generating means actuable in response to operation of the timer for generating an audible signal of relatively short duration at times corresponding to the start of an exercise period, and an audible signal of longer duration at times corresponding to the start of a rest period. In the preferred embodiment the longer audible signal has a duration of fifteen seconds so that a pulse count observed during the signal when multiplied by four gives the patient's pulse rate in beats per minute.

7 Claims, 5 Drawing Figures

TIMING DEVICE FOR EXERCISE PROGRAM WITH SIGNALLING MEANS

FIELD OF THE INVENTION

This invention relates to physiotherapy timing and control devices, and is more particularly concerned with a timing device for signalling a patient to perform a prescribed exercise program.

BACKGROUND OF THE INVENTION

The survivors of the approximately one million Americans who are stricken each year with heart attacks, and those who may be next in line for heart attack, can be helped by proper exercise therapy. Doctors have established that properly prescribed exercises such as walking, exercycling, jogging and swimming contribute significantly to rebuilding the cardiovascular capacity. Following a comprehensive evaluation of the heart patient's maximum exercise stress level, physicians are able to tailor a precise exercise program for the patient consistent with the test data. For maximum effectiveness, and to minimize risk to the patient, the exercise program must be accurately monitored, usually by the patient himself, and a record made of his pulse rate at prescribed times during the exercise program. For the pulse rate reading to be meaningful, it is necessary to maintain uniform, dependable and accurately timed conditions under which the pulse rate is observed and recorded, and in order that the timing of the exercise periods and recording of the pulse rate not interfere with the exercise being performed, the patient should not have to keep his eye on a watch or other timepiece to determine the "start" and "stop" of the exercise periods, nor observe the sweep second hand of a watch while reading his pulse in order to get an accurate pulse rate count. Since a typical exercise program may have a total duration of about forty minutes consisting of a "warm-up period" of ten minutes, a "heart stress" period divided into five "exercise" periods alternating with a like number of "rest" periods during a portion of each of which the pulse rate is observed, and a "cool down" period, the above-outlined method of monitoring the program would be especially cumbersome.

It is an object of the present invention to provide an improved device for monitoring and instructing a patient to perform a prescribed exercise program, such as a cardiovascular stress exercise program.

BRIEF DESCRIPTION OF THE INVENTION

Briefly, the physiotherapy control device according to the invention includes a spring driven timer provided with a color-encoded time-graduated dial to provide visual guidance concerning the steps of a cardiovascular stress exercise program, and also including tone signal generating means actuated by the timer for producing audible signals synchronized with the time intervals presented on the graduated dial. The dial provides a visual indication of the running process of the exercise program, and the timed audible tone signals supplement the visual guidance, or can be utilized independently of the visual guidance, to monitor the exercise program without the patient having to give close visual attention to its progress.

Generation of the timed tone signals is controlled by a pair of cams, driven by the timer motor which actuate respective switches for controlling actuation of a timing module which, in turn, controls a buzzer or the like to produce audible signals of predetermined duration. In the embodiment to be described, signals of one second duration are generation at times corresponding to the start of an exercise period, and signals of 15 seconds duration are generated at times corresponding to the end of an exercise period (or start of a rest period), the latter establishing a finite interval during which the patient observes his pulse. Multiplication by four of the count observed during the 15 second interval gives pulse rate in beats per minute.

BRIEF DESCRIPTION OF THE DRAWINGS

Other objects, features and advantages of the invention, and a better understanding of its construction and operation, will be had from the following detailed description, taken in conjunction with the accompanying drawings, in which.

DESCRIPTION OF THE PREFERRED EMBODIMENT

Figure 1:
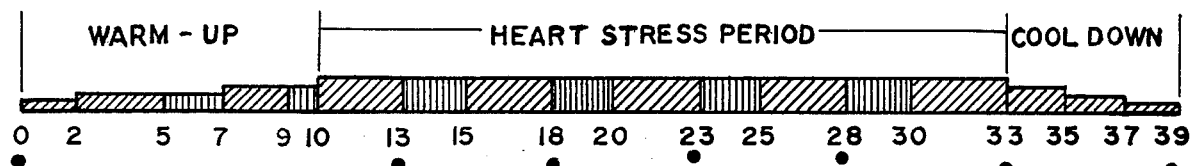
FIG. 1 is a diagram illustrating the steps of a typical cardiovascular stress exercise program.

FIG. 1 depicts a typical cardiovascular stress exercise program which the device of this invention is intended to monitor and control. The program has a total duration of 39 minutes, divided into three stages: a "warm-up" of 10 minutes, a "heart stress" period of 23 minutes and a "cool down" period of 6 minutes. Assuming, by way of example, an exercise program to be performed on an Exercycle, the pulse is read at 0 time after which exercise commences at a first setting of the Exercycle brake (which establishes a stress level prescribed by the physician) which continues for 2 minutes whereupon the stress level is increased, while continuing to exercise, to a second higher step of stress level, with exercise continuing at this level for 3 minutes. This is followed by a 2-minute rest period, during which the stress is adjusted to a third higher stress level at which exercise continues for a period of 2 minutes, followed by a 1-minute rest period. During this rest period the brake is adjusted to maximum stress level, and at the end of the rest period the actual heart stress exercise begins. During the next 23 minutes alternate 3 minutes of exercise and 2 minutes of rest is repeated 5 times, with the pulse read at the end of each of the 5 exercise periods and recorded for future analysis by the physician. The final 6-minute "cool down" period is achieved in three steps of stress reduction, each of 2 minutes duration—a reverse of the "warm-up" process. A final pulse reading is taken at the end of the program, namely, at a time 39 minutes from the start of the program.

It will be appreciated that FIG. 1 describes a particular one of several categories of cardiovascular stress exercise; programs differing in their total time and interval structure might be more suitable for other patients. It is to be understood, also, that programs for forms of exercise other than the exercycle, such as walking, jogging and swimming, similarly achieves heart stress by proceeding through a warm-up period, an actual heart stress period and cool down period following a regimen the same as or similar to that depcited in FIG. 1. It is the function of the present device to visually and/or audibly signal the beginning and end of the timed intervals of the exercise program to signal when in the program the pulse is to be read, and to establish a time interval during which the user is to read his pulse.

Figure 2:
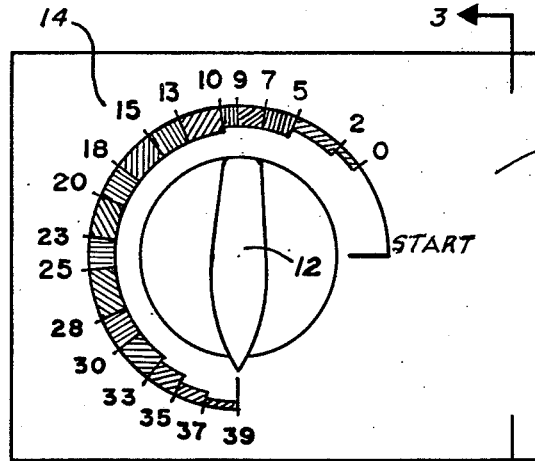
FIG. 2 is an elevation view of the front panel of a device according to one embodiment of the invention, illustrating its time-graduated dial.

Turning now to the other figures, the base timing function of the device is achieved by a spring-wound timer, many types of which are commercially available, having a motor 10 which is hand-wound in the clockwise direction as viewed in FIG. 2 to a "start" position, by a knob 12, which also serves as a pointer which cooperates with an arcuate dial 14 affixed to the front face of a cover plate forming one wall of a generally cubical enclosure. To accomodate the 39 minute exercise program depicted in FIG. 1, the timer is preferably of the 60-minute type. In accordance with one feature of the invention, the dial 14 is time-graduated in intervals corresponding to the intervals of the exercise program depicted in FIG. 1 so that the user can tell from the position of the pointer knob 12 on the dial 14 at what point he is in his exercise program. Ourtqer visual guidance is provided by distinguishing the "exercise" intervals from the "rest" intervals by the use of different colors, for example, green for the exercise periods and red for the rest periods. Thus, the sectors between 0 and 2, between 2 and 5, and between 7 and 9 are green, and the intervals between 5 and 7 and between 9 and 10 are red, and so on, and in order that the individual sectors provide instruction as to the stress level to be applied during their corresponding time intervals, the radial dimension of the sectors are proportional to the applied stress level. For example, the small radial dimension of the sector between 0 and 2 signifies the first step of stress level, the somewhat larger radial dimension of the sector between 2 and 5 signifies the somewhat higher stress level of the second step, the still larger radial dimension of the sector between 7 and 9 signifies the third step of stress level, and the still larger radial dimension of the sector between 10 and 13 (and all of the other "exercise" sectors in the period between 10 and 33) depict the maximum stress level at which the actual heart stress exercise is performed. Similarly, the radial dimension of the sectors between 33 and 35, between 35 and 37, and between 37 and 39 is increasingly smaller to depict the reduction of the stress level, in three steps, during the "cool down" period of the exercise program. Thus, the time graduations of the dial, the color coding of the "exercise" and "rest" periods, and the differences in the radial dimension of the sectors between the time graduations, provide visual guidance of the progress of the exercise program. Knowing that his pulse rate is to be read at the end of the "exercise" periods during the "heart stess" period of the program, the patient can, in the event the battery of the device fails and cannot be immediately replaced, perform the prescribed program of exercise under visual guidance, needing in addition to the present device only a suitable timepiece for establishing the time intervals during which he is supposed to read his pulse.

Figure 5:
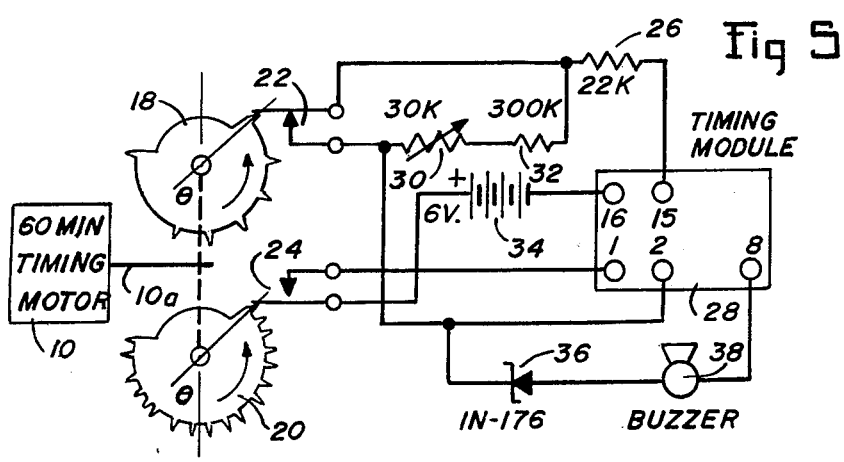
FIG. 5 is a schematic diagram of the circuitry contained in the device of FIGS. 2, 3 and 4.

To supplement the visual guidance afforded by the color-coded, time-graduated dial, or to be used in lieu thereof, the device further includes means for generating audible signals synchronized with the time graduations on the dial 14, a short duration signal, for example, of one second, for signalling the start of an "exercise" period and a longer duration signal, preferably of 15 seconds duration, for signalling the start of "pulse-read" periods and also providing a precise time interval during which the user's pulse is read. Generation of these signals is initiated by a pair of cams 18 and 20 secured to the shaft 10a of the time motor 10 at the end thereof opposite from knob 12, the cams being interlocked in phase and driven in rotation counter-clockwise as viewed in FIG. 5, by the timer motor. As shown, the cams are of flat, disc-shape and each has a plurality of teeth distributed with different predetermined spacings about its periphery; they are conveniently fabricated by removal of selected teeth from a gear having a predetermined number of teeth uniformly distributed around its periphery. For example, the cams can be made by removing appropriate ones of the teeth of a commercially available gear having 60 uniformly spaced teeth, the spacing between successive ones of which represent a time interval of 1 minute if the gear is driven in rotation at one revolution per hour, as occurs if it is driven by a 60-minute timer. As best seen in FIG. 5, cam 18 has fewer teeth than cam 20, the teeth on cam 18 being spaced in correspondence with the times during the heart stress program at which the 15-second signal is to be generated, namely, at 0, 13, 18, 23, 28, 33 and 39 minutes, the cam being shown at the 0 position in FIG. 5; it has no teeth along that portion of its periphery corresponding to the time interval between 39 minutes and 0 on the time-graduated dial 14. Cam 20 also has a tooth at 0, and 17 additional teeth, six of which are phased with corresponding teeth of cam 18, with the remaining 11 spaced to correspond to the times during the exercise program at which the 1-second duration signal is to be generated; i.e., at 2, 5, 7, 9, 10, 15, 20, 25, 30, 35 and 37 minutes.

As the cams 18 and 20 are rotated together, their teeth actuate respective switches 22 and 24, the contacts of which are normally closed and normally open, respectively. The switches are so assembled and the cams so phased that when cam 18 has a tooth phased with a corresponding tooth on cam 20 the cam 18 actuates (opens) switch 22 a small fraction of a second before switch 24 is closed to apply energizing potential to an electronic timing module 28, which may be of the type available in integrated circuit form from Hi-G, Inc., Avon, Conn.; as their Model 6305-230. Without here going into the circuitry of the timing module, suffice to say that when it is energized from a 6 volt battery 34 having its positive and negative terminals connected to pins 1 and 16, respectively, it produces a signal at pin 8 of a time duration proportional to the resistance connected across pins 2 and 15. For example, at those times when the contacts of switch 24 are closed by cam 20 and switch 22 remains closed, only the 22K resistor 26 is connected across pins 2 and 15, and the timing module generates a signal of 1-second duration. However, at those times when switch 22 is opened a small fraction of a second prior to closure of switch 24, a variable 30K resistor 30 and a 300K resistor 32 are placed in series with resistor 26 across pins 2 and 15, the timing module under this condition generating at pin 8 a signal of 15 seconds duration. The purpose of variable resistor 30 is to enable precise adjustment of the 15-second interval regardless of variations in the normal tolerances of resistors 26 and 32 and associated variations in timing module 28. A buzzer 38 and a Zener diode 36, such as an 1N-746, are connected between pin 8 and the fixed contact of switch 24, the buzzer being operative when switch 24 is closed to generate audible signals of either 1-second or 15-seconds duration, depending on the duration of the signal generated at pin 8 of the module. It will be seen that 15-second signals are produced only at times when a tooth or cam 20 is phased with a tooth on cam 18; all other teeth on cam 20 cause generation of a 1-second signal.

Figure 3:
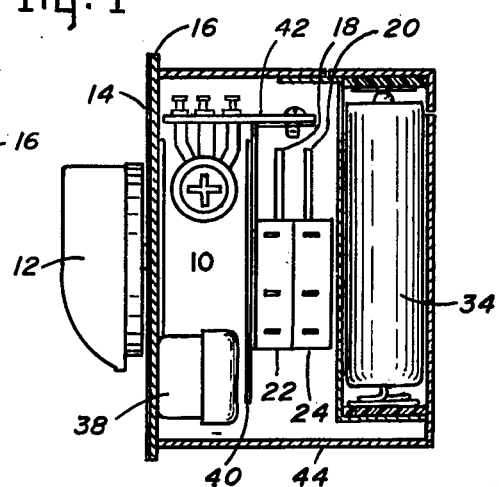
FIG. 3 is a cross-sectional view of FIG. 2, taken along line 3—3.
Figure 4:
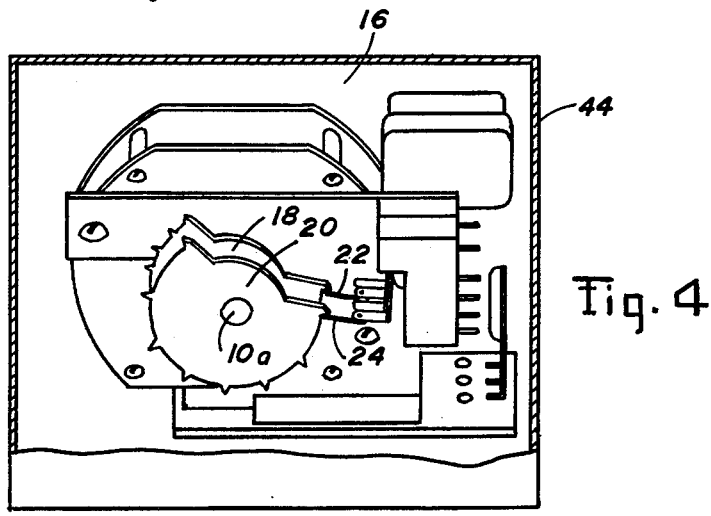
FIG. 4 is an elevation view of the back of the device of FIG. 2, inclined 30° upwardly from the lower rear edge with the enclosure partially cut away to show the arrangement of components within the enclosure.

As seen in FIG. 3 and 4, the buzzer is mounted on the inside surface of cover 16, and switches 22 and 24 are supported on a mounting bracket 30 assembled on the timer motor 10. Resistors 26, 30 and 32, and the timing module 28 are mounted on a circuit board 42, also supported by mounting bracket 40, and the battery 34, which may be four pen-light cells, is mounted in the rear half of housing 44.

The operation of the device, and particularly the circuit of FIG. 5, will be better understood from the following description of its application to the exercise program depicted in FIG. 1. The timer motor 10 is spring wound by turning the knob 12 in the clockwise direction to the "start" position indicated on dial 14, and as the timer motor works its way back to the arbitrarily selected position marked 0, the first tooth on cam 18 opens the contacts of switch 22 and a fraction of a second thereafter the first tooth on cam 20 closes switch 24 so as to generate an audible signal of 15 seconds duration. During this time period, the patient reads his pulse, and then multiplies the observed count by four and records the resulting beats per minute. This reading, then, indicates the patient's pulse rate before the heart stress program is begun. As soon as the pulse is read, the user starts to exercise at a low stress level which is continued for 1 minute and 45 seconds whereupon the second tooth of cam 20 closes the contacts of switch 24 to generate a signal of 1-second duration which alerts the user to increase the stress to the second stress level, while continuing to exercise. Exercise activity continues at the second stress level for 3 minutes at the end of which the third tooth of cam 20 again closes the contacts of switch 24 to generate a 1-second signal. At this stage of the exercise program, the one-second signal instructs the patient to stop exercising, to adjust the stress to the third step of stress level and to rest until a warning instructs him to resume exercise. In the program of FIG. 1, the "rest" period is of 2 minutes duration, at the end of which the fourth tooth of the cam 20 again closes the contacts of switch 24, to generate the 1-second warning signal. Exercise at the third stress level continues for 2 minutes, at the end of which the fifth tooth on cam 20 generates another 1-second signal instructing the patient to stop exercising, to adjust the stress level to maximum and to rest until the next 1-minute signal. At the end of this 1-minute "rest" period a warning signal of 1-second duration is generated to signal the start of the actual heart stress exercise.

The next 23 minutes consist of alternate 3 minutes "exercise" and 2 minutes "rest". At the end of each exercise period, this is, at times of 13, 18, 23, 28 and 33, cam 18 has a tooth phased with a tooth on cam 20 (indicated by the dots on the timing diagram of FIG. 1) which causes generation of a signal of 15-seconds duration, during which the patient reads his pulse, multiplies the observed number by four and records the actual pulse rate in beats per minute. At the end of the 30–33 minute interval, the 15-second signal also instructs the patient to reduce the stress level, and at the end of the first 2-minute segment of the "cool down" period another 1-second-duration signal is generated to instruct further reduction of the stress level to the next lower step. Two minutes later another 1-second signal instructs the patient to again reduce the stress level. At the end of the exercise program (total elapsed time of 39 minutes) cam 18 has a tooth phased with a tooth on cam 20 so as to generate a 15-seconds-duration signal during which the pulse is read, multiplied by four, and recorded. Thus, it is seen that a patient having some familiarity with the exercise program he is to perform is guided through the exercise programs by distinctive audible signals synchronized with the dial of the timer, making it unnecessary for him to watch the timer dial or use a watch to read his pulse.

Although the invention has been described in connection with one particular cardiovascular stress exercise program, it will be appreciated that other programs differing in total time duration and interval structures may be prescribed for heart stress conditions different from those for which the described program was prescribed. Other such programs can be readily accomodated by designing and affixing to the timer, a dial 14 which conforms to the program and providing another set of cams 18 and 20 each having teeth properly distributed so as to synchronize the generation of the 1-second and 15-second signals in synchronism with the time-graduated dial.

The described device is sufficiently small and light in weight as to be conveniently carried on the user's belt when walking or jogging, and is also conveniently mounted on the handlebars of an Exercycle. The signal generated by the buzzer is sufficiently loud as to be heard at some distance so that should the prescribed exercise program involve swimming, for example, the device can be placed at the side of a pool and yet be effective in instructing the user in what to do at prescribed intervals.

What is claimed is:

1. Apparatus for instructing a patient to perform a prescribed program of exercise including a series of "exercise" periods each followed by a "rest" period at the start of which the patient is required to read and record his pulse rate, said apparatus comprising, in combination, spring-wound timer means having a timing cycle at least as long as the prescribed exercise program and a timer motor having a shaft to one end of which is secured a winding knob which also serves as a pointer, a dial supported in cooperative relationship with said knob, said dial being time-graduated in intervals corresponding to the intervals of the prescribed exercise program, and signal generating means including cam-controlled switches operative in response to the operation of said timer means for generating first and second audible signals of predetermined durations at times synchronized with the time graduations on said dial, the first signal generated at the times corresponding to the start of a "rest" period having a duration equal to a sub-multiple of 60 seconds thereby establishing a period during which the patient reads his pulse which reading when multiplied by said multiple gives his pulse rate in beats per minute, and the second signal generated at the times corresponding to the start of an "exercise" interval having a duration substantially shorter than the first signal.

2. Apparatus according to claim 1, wherein said first audible signal has a duration approximately equal to 15 seconds and said second signal has a duration approximately equal to 1 second.

3. Apparatus according to claim 1, wherein said signal generating means is controlled by electronic timing means energizable from a battery, and first and second toothed cams supported on and driven in rotation by the shaft of said timer motor, the teeth on said first and second cams being differently spaced as determined by the desired time of initiation of said first and second audible signals and arranged to actuate first and second switches.

4. Apparatus according to claim 3, wherein said first switch is normally open and when closed by a tooth on said first cam is operative to energize said electronic timing means to generate said second audible signal, and wherein said second switch is normally closed and when its contacts are opened by a tooth on said second cam a small fraction before the contacts of said first switch are closed by a tooth on said first cam, said electronic timing means is energized to generate said first audible signal.

5. Apparatus according to claim 4, wherein said first audible signal has a duration approximately equal to 15 seconds and said second audible signal has a duration approximately equal to 1 second.

6. Apparatus according to claim 1, wherein the intervals on said time-graduated dial corresponding to "exercise" periods of said exercise program are distinguished by a first color and the intervals of said time-graduated dial corresponding to "rest" periods of said exercise program are distinguished by a second color.

7. Apparatus according to claim 6, wherein the intervals on said time-graduated dial corresponding to "exercise" periods of said exercise program have indicia between the time-graduations defining the intervals having differing radial dimensions for signifying the stress level at which the exercise is to be performed during each of the "exercise" periods.

* * * * *

UNITED STATES PATENT AND TRADEMARK OFFICE
CERTIFICATE OF CORRECTION

PATENT NO. : 3,973,251
DATED : August 27, 1976
INVENTOR(S) : J. LARRY STEPHANS

It is certified that error appears in the above-identified patent and that said Letters Patent are hereby corrected as shown below:

Cover sheet, last name of inventor should be -- STEPHANS --.

Signed and Sealed this

Nineteenth Day of October 1976

[SEAL]

Attest:

RUTH C. MASON
*Attesting Officer*

C. MARSHALL DANN
*Commissioner of Patents and Trademarks*